United States Patent
Wendel et al.

(10) Patent No.: US 7,244,417 B2
(45) Date of Patent: *Jul. 17, 2007

(54) STABILIZATION OF OXIDATION-SENSITIVE OR UV-SENSITIVE ACTIVE INGREDIENTS

(75) Inventors: Volker Wendel, Hamburg (DE); Anja Göppel, Hamburg (DE)

(73) Assignee: Beiersdorf AG, Hamburg (DE)

( * ) Notice: Subject to any disclaimer, the term of this patent is extended or adjusted under 35 U.S.C. 154(b) by 302 days.

This patent is subject to a terminal disclaimer.

(21) Appl. No.: 10/788,607

(22) Filed: Feb. 27, 2004

(65) Prior Publication Data

US 2004/0247538 A1 Dec. 9, 2004

Related U.S. Application Data

(63) Continuation of application No. PCT/EP02/09375, filed on Aug. 22, 2002.

(30) Foreign Application Priority Data

Aug. 29, 2001 (DE) ................. 101 41 477

(51) Int. Cl.
 A61K 8/00 (2006.01)
 A61K 8/04 (2006.01)
 A61K 31/53 (2006.01)
 A61Q 17/00 (2006.01)
 A61Q 17/04 (2006.01)
 A61Q 19/00 (2006.01)

(52) U.S. Cl. .................. 424/59; 424/60; 424/400; 424/401; 514/241

(58) Field of Classification Search .............. 424/59, 424/60, 400, 401; 514/241
See application file for complete search history.

(56) References Cited

U.S. PATENT DOCUMENTS

| | | | |
|---|---|---|---|
| 5,993,789 A | 11/1999 | Bonda et al. | |
| 6,113,931 A | 9/2000 | Bonda et al. | |
| 6,126,925 A | 10/2000 | Bonda et al. | |
| 6,129,909 A | 10/2000 | Bonda et al. | |
| 6,180,091 B1 | 1/2001 | Bonda et al. | |
| 6,284,916 B1 | 9/2001 | Bonda et al. | |
| 6,355,230 B2 * | 3/2002 | Gers-Barlag et al. | 424/59 |
| 6,355,261 B1 | 3/2002 | Bonda et al. | |
| 6,368,578 B1 * | 4/2002 | Gers-Barlag et al. | 424/59 |
| 6,403,067 B1 | 6/2002 | Schamper et al. | |
| 6,440,402 B1 * | 8/2002 | Gonzalez et al. | 424/59 |
| 6,468,511 B1 | 10/2002 | Chopra et al. | |
| 6,491,901 B2 * | 12/2002 | Gers-Barlag et al. | 424/59 |
| 2001/0022966 A1 | 9/2001 | Gers-Barlag et al. | |
| 2001/0026790 A1 | 10/2001 | Gers-Barlag et al. | |
| 2002/0164296 A1 | 11/2002 | Schamper et al. | |
| 2002/0192172 A1 | 12/2002 | Chopra et al. | |

| | | |
|---|---|---|
| 2003/0170284 A1 | 9/2003 | Dorschner et al. |

FOREIGN PATENT DOCUMENTS

| | | |
|---|---|---|
| DE | 199 49 825 A1 | 4/2001 |
| FR | 2 801 206 A | 5/2001 |
| FR | 2 801 207 A | 5/2001 |
| FR | 2 801 208 A | 5/2001 |
| FR | 2 801 209 A | 5/2001 |
| FR | 2 801 210 A1 | 5/2001 |
| FR | 2 801 213 A1 | 5/2001 |
| GB | 660131 A | 10/1951 |
| WO | WO 02 17873 A | 3/2002 |

OTHER PUBLICATIONS

"Illinois Researcher Receives Award for Developing a Better Sunscreen," EurekAlert! released Jun. 7, 2001 (http://www.eurekalert.org).

"Beauty is Skin Deep," Household and Personal Products Industry (HAPPI), posted online Sep. 2000 (http//www.happi.com/special/sep002.htm).

International Search Report from corresponding International Application No. PCT/EP02/08577, dated Dec. 20, 2002.

German Search Report dated Mar. 27, 2002 for German Application No. DE 101 41 472.2.

(Continued)

*Primary Examiner*—Shelly A. Dodson
(74) *Attorney, Agent, or Firm*—Greenblum & Bernstein, P.L.C.

(57) ABSTRACT

The cosmetic or dermatological formulations of the invention include:

(a) at least one oxidation-sensitive or UV-sensitive active ingredient,
(b) at least one dialkyl naphthalate which is distinguished by the structural formula

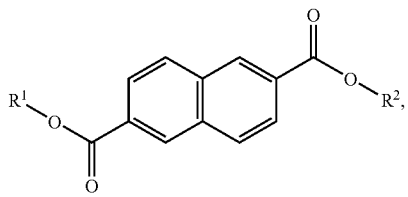

in which $R^1$ and $R^2$, independently of one another, are chosen from the group of branched and unbranched alkyl groups having 6 to 24 carbon atoms, and (c) at least one wax and/or one oil thickener.

The present invention also includes methods of using the cosmetic or dermatological formulations.

33 Claims, No Drawings

OTHER PUBLICATIONS

German Search Report dated Apr. 12, 2002 for German Application No. DE 101 41 473.0.
Bonda C Et Al: "A New Photostabilizer For Full Spectrum Sunscreens" Cosmetics & Toiletries, Wheaton, IL, US, vol. 115, No. 6, 2000, pp. 37-45.
International Search Report from corresponding International Application No. PCT/EP02/09309 dated Sep. 30, 2003.
International Search Report from corrseponding International Application No. PCT/EP02/09374 dated Sep. 30, 2003..
International Search Report from corresponding International Application No. PCT/EP02/09375 dated Dec. 10, 2002.
International Search Report from corresponding International Application No. PCT/EP02/09567, dated Sep. 30, 2003.
International Search Report from corresponding International Application No. PCT/EP02/09543 dated Oct. 2, 2003..
International Search Report from corresponding International Application No. PCT/EP02/009310 dated Apr. 12, 2002.
German Search Report for 101 41 474.9 dated Apr. 15, 2002.
German Search Report for 101 41 478.1 dated Apr. 15, 2002.
German Search Report for 101 41 475.7 dated Jul. 19, 2002.

* cited by examiner

STABILIZATION OF OXIDATION-SENSITIVE OR UV-SENSITIVE ACTIVE INGREDIENTS

CROSS-REFERENCE TO RELATED APPLICATIONS

This is a continuation application of PCT/EP02/09375, filed Aug. 22, 2002, which is incorporated herein by reference in its entirety, and also claims the benefit of German Priority Application No. 101 41 477.3, filed Aug. 29, 2001.

FIELD OF THE INVENTION

The present invention relates to substance combinations for stabilizing oxidation-sensitive and/or UV-sensitive active ingredients, and to cosmetic and dermatological formulations containing oxidation-sensitive and/or UV-sensitive active ingredients stabilized in this way. In particular, it relates to cosmetic and dermatological photoprotective formulations and formulations with UV-sensitive photoprotective filter substances which are stabilized through the use of these substance combinations.

BACKGROUND OF THE INVENTION

The harmful effect of the ultraviolet part of solar radiation on the skin is generally known. The rays have different effects on the skin organ depending on their particular wavelength: so-called UV-C radiation with a wavelength below 290 nm is absorbed by the ozone layer in the earth's atmosphere and therefore is of no physiological importance. By contrast, rays in the range between 290 nm and 320 nm, the so-called UV-B region, cause erythema, simple sunburn or even burns of greater or lesser severity. A maximum for the erythema activity of sunlight is stated as being the relatively narrow range around 308 nm.

Numerous compounds are known for protecting against UV-B radiation, examples thereof being derivatives of 3-benzylidenecamphor, of 4-aminobenzoic acid, of cinnamic acid, of salicylic acid, of benzophenone, and of triazine.

It has long been incorrectly assumed that the long-wave UV-A radiation with a wavelength between 320 nm and 400 nm has only a negligible biological effect. However, it has now been proven by numerous studies that UV-A radiation is far more hazardous than UV-B radiation with regard to the triggering of photodynamic, specifically phototoxic, reactions and chronic changes in the skin. The harmful effect of UV-B radiation can also be further intensified by UV-A radiation.

Thus, it has been proven, inter alia, that even UV-A radiation under entirely normal everyday conditions is sufficient to damage within a short time the collagen and elastin fibers which are of essential importance for the structure and firmness of the skin. This results in chronic photoinduced changes in the skin - the skin "ages" prematurely. The clinical appearance of skin aged by light includes, for example, wrinkles and lines and an irregular, furrowed relief. In addition, the areas affected by photoinduced skin aging may have irregular pigmentation. The formation of brown spots, keratoses and even carcinomas or malignant melanomas is also possible. Skin aged prematurely by everyday exposure to UV is additionally characterized by a lower activity of the Langerhans cells and a slight chronic inflammation.

Approximately 90% of the ultraviolet radiation which reaches the earth consists of UV-A rays. Whereas UV-B radiation varies greatly depending on numerous factors (for example time of year and time of day or latitude), UV-A radiation remains relatively constant from day to day irrespective of seasonal and diurnal or geographic factors. At the same time, most of the UV-A radiation penetrates into the living epidermis, while about 70% of the UV-B rays are retained by the horny layer.

It is therefore of fundamental importance that cosmetic and dermatological photoprotective preparations provide adequate protection both against UV-B and against UV-A radiation.

In general, the light absorption behavior of photoprotective filter substances is very well known and documented, especially since most industrialized countries have positive lists for the use of such substances, which impose very strict standards on the documentation.

However, the concentration in which known photoprotective filter substances present as solids are used is often restricted—in particular in combination with other substances which are to be dissolved. There are thus certain technical difficulties with regard to formulating in achieving relatively high sun protection factors and UV-A protection performance.

Advantageous UV-A filter substances are e.g. dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

The main disadvantage of all dibenzoylmethane derivatives which absorb in the UV region is a certain instability toward UV radiation, meaning that these components are decomposed under the influence of UV to give inactive products and are no longer available for UV absorption. Preparations of the prior art with a content of these substances therefore expediently also comprise certain UV stabilizers such as, for example, ethylhexyl 2-cyano-3,3-diphenylacrylate (octocrylene) or 4-methylbenzylidenecamphor.

The prior art also recognizes a series of different efficient, lipophilic skincare active ingredients—such as, for example, ubiquinones, retinoids and carotenoids—which contain unsaturated, aromatic or benzoidal structural elements, the use of which in cosmetic or dermatological formulations, in particular in formulations of the oil-in-water type, is very desirable. Unfortunately, however, substances of this kind are often very unstable meaning that, particularly in aqueous media, they rapidly decompose and thereby lose their effectiveness.

SUMMARY OF THE INVENTION

An object of the present invention was to overcome the disadvantages of the prior art and to arrive in a simple manner at preparations which are distinguished by a high UV, in particular UV-A, protection performance and in which the use of customary UV stabilizers can be dispensed with.

It was therefore a further object of the present invention to increase the stability of oxidation-sensitive and/or UV-sensitive active ingredients, and to provide stable preparations with oxidation-sensitive and/or UV-sensitive active ingredients whose effectiveness is retained over a long period.

It was surprising and could not have been foreseen by the person skilled in the art that cosmetic and dermatological formulations containing at least one oxidation- and/or UV-sensitive active ingredient, characterized in that they comprise
  (a) at least one dialkyl naphthalate which is distinguished by the structural formula

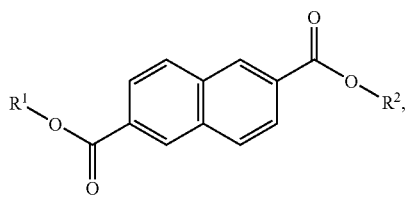

in which $R^1$ and $R^2$, independently of one another, are chosen from the group of branched and unbranched alkyl groups having 6 to 24 carbon atoms, and
  (b) at least one wax and/or one oil thickener overcome the disadvantages of the prior art.

If the oxidation- and/or UV-sensitive active ingredient(s) are present in a formulation according to the invention, then they are protected in an excellent manner against the decomposition induced by UV radiation. This is true in particular for dibenzoylmethane derivatives.

The invention therefore also provides for the use of substance combinations which comprise
  (a) at least one dialkyl naphthalate which is distinguished by the structural formula

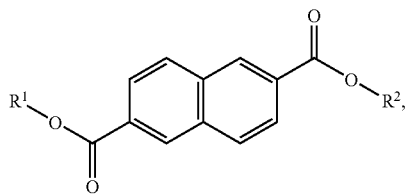

in which $R^1$ and $R^2$, independently of one another, are chosen from the group of branched and unbranched alkyl groups having 6 to 24 carbon atoms, and
  (b) at least one wax and/or one oil thickener for stabilizing cosmetic or dermatological active ingredients against decomposition induced by UV radiation.

DETAILED DESCRIPTION OF THE PREFERRED EMBODIMENTS

As well as one or more oil phases, the preparations within the meaning of the present invention may preferably additionally comprise one or more water phases and be present, for example, in the form of W/O, O/W, W/O/W or O/W/O emulsions. Such formulations may preferably also be a microemulsion, a PIT emulsion, a water-containing or anhydrous stick formulation, a solid emulsion (i.e. an emulsion which is stabilized by solids, e.g. a Pickering emulsion), a sprayable emulsion or a hydrodispersion.

The preparations according to the invention are entirely satisfactory preparations in every respect which are not restricted to the limited choice of raw materials. Accordingly, they are very particularly suitable for use as bases for preparation forms with diverse application purposes. The preparations according to the invention exhibit very good sensory and cosmetic properties, such as, for example, extensibility on the skin or the ability to absorb into the skin, and are further distinguished by very good photoprotection effectiveness coupled with excellent skincare data.

It was particularly surprising that with the use according to the present invention it is possible to dispense entirely with the use of further UV stabilizers, in particular with the use of ethylhexyl 2-cyano-3,3-diphenylacrylate (octocrylene) or 4-methylbenzylidenecamphor.

In addition, the use according to the invention surprisingly allows the stability of lipophilic active ingredients in anhydrous cosmetic or dermatological formulations, in particular in O/w formulations, to be considerably increased compared with the prior art.

The invention thus also provides for the use of substance combinations which comprise
  (a) at least one dialkyl naphthalate which is distinguished by the structural formula

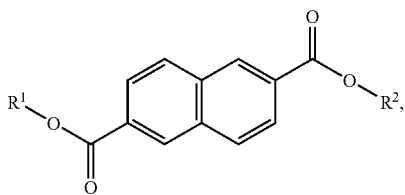

in which $R^1$ and $R^2$, independently of one another, are chosen from the group of branched and unbranched alkyl groups having 6 to 24 carbon atoms, and
  (b) at least one wax and/or one oil thickener for improving the effectiveness and increasing the stability of lipophilic active ingredients in cosmetic or dermatological preparations.

Advantageous lipophilic active ingredients which are stabilized in an excellent manner by the use according to the invention are those whose log P value is greater than 3.5. P is the partition coefficient, which is defined as the ratio of the equilibrium concentration of a dissolved substance in a two-phase system which consists of two solvents which are essentially immiscible with one another. These two solvents are, in the present case, n-octanol and water, i.e.

$$P_{ow} = \frac{c_{n-octanol}}{c_{water}}$$

It is advantageous for the purposes of the present invention to choose the lipophilic active ingredients from the group of ubiquinones and plastoquinones. For the purposes of the present invention, coenzyme Q10, which has a log P value of about 15, is very particularly advantageous.

It was particularly surprising that very advantageous preparations according to the present invention can be obtained when the active ingredient(s) is/are chosen only from the group of ubiquinones.

Further lipophilic active ingredients which are advantageous according to the invention are retinoids (vitamin A acid and/or derivatives thereof) or vitamin A and/or derivatives thereof. The group of retinoids advantageous according to the invention is defined as including all cosmetically and/or pharmaceutically acceptable retinoids, including retinol and its esters, retinal and also retinoic acid (vitamin A acid) and esters thereof. For the purposes of the present invention, retinol (with a log P value of about 7) and retinyl palmitate (with a log P value of about 13) are particularly advantageous.

It was also particularly surprising that very advantageous preparations can be obtained according to the present invention when the active ingredient(s) is/are chosen only from the group of retinoids.

Further lipophilic acid ingredients advantageous according to the invention are carotenoids. For the purposes of the present invention, β-carotene, which has a log P value of 15, for example, is particularly advantageous.

Further lipophilic active ingredients advantageous according to the invention are:
lipoic acid and derivatives,
vitamin E and derivatives,
vitamin F,
dioic acid [8-hexadecene-1,16-dicarboxylic acid (CAS number 20701-68-2)]

The amount of lipophilic active ingredients (one or more compounds) in the preparations is preferably 0.0001 to 10% by weight, particularly preferably 0.001 to 5% by weight, based on the total weight of the preparation.

Advantageous for the purposes of the present invention are dialkyl naphthalates in which $R^1$ and/or $R^2$ are branched alkyl groups having 6 to 10 carbon atoms. Very particular preference for the purposes of the present invention is given to diethylhexyl naphthalate, which is obtainable, for example, under the trade name Hallbrite TQ™ from CP Hall or Corapan TQ™ from H&R.

According to the invention, cosmetic or dermatological preparations advantageously comprise 0.001 to 20% by weight, preferably 0.01 to 15% by weight, very particularly preferably 1 to 15% by weight, of one or more dialkyl naphthalates.

Waxes:

In accordance with the stipulations of the Deutsche Gesellschaft für Fettwirtschaft [German Society for Fat Commerce] (*Fette, Seifen, Anstrichmittel*, 76, 135 [1974]), to designate the term "wax" usually involves taking into consideration the mechanical-physical properties of the waxes, that are relevant for their use, while the particular chemical composition is not taken into account for the definition.

"Wax"—like "resin"—is a collective term for a series of natural or synthetic substances which usually have the following properties: kneadable at 20° C., solid to brittlely hard, coarsely to finely crystalline, transparent to opaque, but not glass-like, melt above 40° C. without decomposition, even a little above the melting point are relatively low-viscosity and not thread-drawing, have a considerable temperature-dependent consistency and solubility and can be polished under slight pressure. If, in borderline cases, a substance does not satisfy more than one of the abovementioned properties, then it is not a wax within the meaning of this definition. Waxes differ from similar synthetic or natural products (e.g. resins, plastic masses etc.) primarily by virtue of the fact that they convert to the molten, low-viscosity state usually between about 30 and 90° C., in exceptional cases also up to about 200° C. and are virtually free from ash-forming compounds.

Oil thickeners are substances which, for example, are able to take up liquid oils and form homogeneous, viscous and colloidal solutions. They are added to cosmetic or dermatological preparations during their preparation or processing in order to thicken the fatty phase.

Waxes and/or oil thickeners for the purposes of the present invention are compounds which are characterized in that, together with the other oil components of the preparations according to the invention (such as, for example, polar, liquid compounds, UV filters and solvents thereof etc.), they form a mass which is spreadable or flowable at room temperature and which, at 20° C., has a viscosity of more than 500 mPa·s.

Advantageous according to the invention are, for example, natural waxes of animal and vegetable origin, such as, for example, beeswax, Chinese wax, bumble-bee wax and other insect waxes, in particular those specified above.

Beeswax, for example, is an excretion product from the glands of honey bees which the latter use to build honeycombs. Yellow (Cera flava), brown or red so-called crude wax is, for example, obtainable by melting the honeycombs freed from the honey by centrifugation, separating the melt from solid impurities, and allowing the resulting crude wax to solidify. The crude wax can be bleached completely white using oxidizing agents (Cera alba).

Beeswax consists of cerin, which is readily soluble in alcohol and is a mixture of cerotic acid $CH_3(CH_2)_{24}COOH$ and melissic acid $CH_3(CH_2)_{28}COOH$, and of an ester mixture termed myricin consisting of about 70 esters of $C_{16}$- to $C_{36}$-acids and $C_{24}$- to $C_{36}$-alcohols. The essential constituents of beeswax are myricyl palmitate, myricyl cerotinate and paraffin.

Other insect waxes, such as, for example, bumble-bee wax, shellac wax or Chinese wax, are also essential mixtures of various esters. Chinese wax, for example, is deposited or produced in China and Japan from the wax scale louse (Coccus ceriferus) living on the Chinese ash, and the scale louse species Ceroplastes ceriferus and Ericerus pela. It is scraped from the trees and purified by remelting in boiling water. The main constituent of Chinese wax is the cerotic ester of ceryl alcohol.

Shellac wax is obtained from lac, the secretion of the female lac insects (*Kerria lacca*), which live in huge colonies (lac is derived from the Hindhi word "Lakh" for 100 000) on trees and shrubs in southern Asia (India, Burma, southern China). The shellac wax obtainable by solvent extraction contains, as essential constituents, myricyl alcohol, melissic acid and other wax alcohols and acids or esters thereof.

Plant waxes are also advantageous for the purposes of the present invention. Those preferably used are cuticular waxes of lower or higher plants, algae, lichens, mosses and fungi, such as, for example, candelilla wax, carnauba wax, Japan wax, esparto grass wax, cork wax, rice wax, sugar cane wax, fruit waxes, e.g. apple wax, flower waxes, leaf waxes from conifers, coffee wax, flax wax, sesame wax, jojoba oil and the like.

Candelilla waxes, for example, are brownish to yellowish brown, hard wax-like masses which are soluble in lipophilic solvents. Candelilla wax contains odd-number aliphatic hydrocarbons (about 42%), esters (about 39%), wax acids and wax alcohols. It can be obtained, for example, from the comminuted fleshy leaves of a thornless spurge species (*Euphorbia cerifera*) by boiling with aqueous sulfuric acid.

Carnauba wax is a yellowish, greenish or dark-gray mass which can be obtained in varying grades, obtained by selection, from the leaves of the Brazilian fan palm *Copernicia prunifera* or carnauba palm (*Carnauba cerifera*) by, for example, brushing the wax dust from the withered fronds, melting it and filtering it and, after solidification, breaking it into pieces. Canauba wax can be lightened by bleaching agents. It contains about 85% esters, in each case about 2-3% free wax acids (carnaubic, behenic, lignoceric, melissic and cerotic acid), long-chain alcohols, diols and saturated hydrocarbons.

Japan wax (also: Japan tallow or Cera japonica) is colorless or yellowish, pure plant fat which can be obtained, for example, in Japan from the fruits of a tree-like sumac plant (*Rhus succedanea*) by boiling. The main constituents of japan wax are palmitic glycerol esters and also esters of japanic acid (heneicosanedioic acid, $C_{21}H_{40}O_4$), of phellogenic acid (docosanedioic acid, $C_{22}H_{42}O_4$) and of tricosanedioic acid ($C_{23}H_{44}O_4$).

Esparto wax is obtained as a by-product in the manufacture of pulp and paper from the esparto grass (Graminaceae) indigenous to Mediterranean countries. It consists of about 15 to 17% of wax acids (e.g. cerotic and melissic acid), of 20 to 22% of alcohols and hydrocarbons, and of 63 to 65% of esters.

Particularly advantageous natural waxes for the purposes of the present invention are, for example, those available under the trade names Permulgin 1550 and Permulgin 4002 from KOSTER KEUNEN, and those available under the trade names Shellac Wax 7302 L and Candelilla Wax 2039 L from KAHL wax refinery.

Also advantageous according to the invention are chemically modified waxes and synthetic waxes. Preferred modified waxes are, for example, beeswax esters, in particular the alkyl beeswaxes available under the trade names BW Ester BW 67, BW Ester BW 80 from KOSTER KEUNEN.

Preferred synthetic waxes are, for example, that available under the trade name beeswax component B 85 from SCHLICKUM, and silicone-based waxes, such as, for example, dialkoxydimethylpolysiloxanes, which are characterized by the following structure

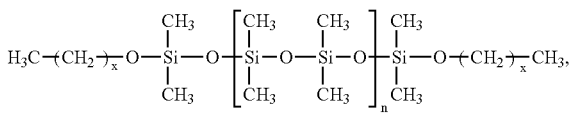

in which x is a number between 18 and 24. Behenoxydimethicone, for which x from the above structural formula is 21 and which is available under the trade name Abil® Wax 2440 from Th. Goldschmidt AG is particularly advantageous. Also preferred according to the invention is a silicone-based wax available under the trade name Siliconyl Beeswax from KOSTER KEUNEN.

Further advantageous synthetic waxes are certain fatty acids and/or fatty acid mixtures, for example $C_{16-36}$-fatty acids, in particular those available under the trade name Syncrowax AW1C from Croda GmbH.

Also advantageous for the purposes of the present invention are ester waxes, which are esters of
1. a saturated and/or unsaturated, branched and/or unbranched mono- and/or dicarboxylic acid having 12 to 40 carbon atoms and
2. a saturated and/or unsaturated, branched and/or unbranched alcohol having 12 to 40 carbon atoms.

Particularly advantageous ester waxes are those chosen from the group listed below:

| Ester wax | Trade name | available from |
|---|---|---|
| Myristyl myristate | Cetiol MM | Henkel KGaA |
| Cetyl palmitate | Cutina CP | Henkel KGaA |
| $C_{14-34}$ Alkyl stearate | Kester wax K 76 H | KOSTER KEUNEN |
| $C_{20-40}$ Dialkyl dimerate | Kester wax K 80 D | KOSTER KEUNEN |
| Ditetracosanyl dimerate | Kester wax K70D | KOSTER KEUNEN |
| $C_{16-38}$ Alkyl hydroxystearoyl stearate | Kester wax K80P | KOSTER KEUNEN |
| $C_{20-40}$ Alkyl stearoylstearoyl stearate | Kester wax K80P-VS | KOSTER KEUNEN |
| $C_{20-40}$ Alkylstearat | Kester wax K 82 | KOSTER KEUNEN |
| Hydroxystearyl hydroxystearate | Elfacos C26 | AKZO NOBEL |

Also advantageous are esters of glycol, in particular glycol esters of lignoceric acid ($CH_3(CH_2)_{22}COOH$), of cerotic acid ($CH_3(CH_2)_{24}COOH$) and/or of montanic acid ($CH_3(CH_2)_{26}COOH$). Very particularly advantageous for the purposes of the present invention are glycol esters of montanic acid ($CH_3(CH_2)_{26}COOH$). An advantageous glycol montanate is available, for example, in a mixture with butylene glycol montanate under the trade name Wax E Pharma from Clariant.

It is also advantageous to choose the wax components from the group of glycerides, in particular from the group of triglycerides. The glycerides and triglycerides listed below are particularly advantageous:

| Glyceride | Trade name | available from |
|---|---|---|
| $C_{16-18}$ Triglyceride | Cremeol HF-52-SPC | Aarhus Oliefabrik |
| Glyceryl hydroxystearate | Naturchem GMHS | Rahn |
| Hydrogenated cocoglycerides | Softisan 100 | Hüls AG |
| Caprylic/capric/isostearic/adipic triglyceride | Softisan 649 | Dynamit Nobel |
| $C_{18-36}$ Triglyceride | Syncrowax HGLC | Croda GmbH |
| Glyceryl tribehenate | Syncrowax HRC | Croda GmbH |
| Glyceryl tri(12-hydroxystearate) | Thixcin R | Rheox/NRC |
| Hydrogenated castor oil | Cutina HR | Henkel KGaA |
| $C_{16-24}$ Triglyceride | Cremeol HF-62-SPC | Aarhus Oliefabrik |

Also of particular preference for the purposes of the present invention is shea butter, also called karité oil or galam butter (CAS No. 68920-03-6). Shea butter is the fat of the seeds or kernels of the plant Butyrospermum Parkii belonging to the family of the *Sapotaceae*, and consists of approximately 34 to 45% by weight of solid fatty acids (principally stearic acid) and of approximately 50 to 60% by weight of liquid fatty acids (principally comprising oleic acid).

According to the invention, the waxes are also preferably chosen from the group of saturated and/or unsaturated, branched and/or unbranched fatty alcohols having 14 to 40 carbon atoms, particular preference being given to behenyl alcohol ($C_{22}H_{45}OH$), cetearyl alcohol [a mixture of cetyl alcohol ($C_{16}H_{33}OH$) and stearyl alcohol ($C_{18}H_{37}OH$)], cetyl arachidol [2-hexadecyl-1-eicosanol ($C_{36}H_{73}OH$),] and/or 2-tetradecyloctadecanol ($C_{32}H_{65}OH$). Advantageous embodiments of the last two mentioned fatty alcohols are available under the trade names Isofol 36 and Isofol 32 from Condea.

For the purposes of the present invention, oil thickeners are chosen, for example, from the group of metal soaps. Metal soaps are the salts of higher fatty, resin and naphthenic acids (stearates, palmitates, oleates, linoleates, resinates, laurates, octanoates, ricinoleates, 12-hydroxystearates, naphthenates, tallates and the like) with the exception of the sodium and potassium salts, i.e. e.g. the salts of the metals aluminum, barium, calcium, cadmium, cobalt, chromium, copper, iron, lithium, magnesium, manganese, nickel, lead, tin, strontium, zinc.

The person skilled in the art of course knows that, among the metal soaps, there are those which would in principle be suitable for realizing the present invention, but which should nevertheless be omitted due to an unacceptable effect on the skin or other accompanying phenomena. According to the CIR panel, a body which checks whether there is adequate toxicity data for substances which are used in the cosmetics industry (CIR: Cosmetic Ingredient Review), lithium stearate, aluminum stearate, calcium stearate and zinc stearate, for example, in the doses which are customarily used for the preparation of cosmetic compositions, are to be regarded as risk-free. As well as satisfying the requirements of various pharmaceutical regulations, magnesium stearate also satisfies the requirements which food grade imposes.

For the sake of simplicity, for a clear distinction between cosmetically acceptable and unacceptable substances, reference is made to the relevant regulations (e.g. Cosmetics Directive, Food and Drugs Act, official pharmacopeia, publications by the CIR panel etc.).

For the purposes of the present invention, particular preference is given to aluminum stearate and magnesium stearate.

In addition, the oil thickener(s) are advantageously chosen from the group of phyllosilicates, in particular from the group of bentonites and hectorites. Bentonites are clays and rocks which contain smectites, especially montmorillonite, as the main minerals. For the purposes of the present invention, particular preference is given to modified bentionites and hectorites, for example those whose organophilicity has been increased by reaction with quaternary ammonium compounds. These types of bentonites are also referred to as organophilic bentonites or bentones. Very particular preference is given to stearalkonium hectorite, a reaction product of hectorite and stearalkonium chloride (benzyldimethylstearylammonium chloride), and quaternium-18 hectorite, a reaction product of hectorite and a quaternary ammonium salt, which are available e.g. under the trade names Bentone 27 and Bentone 38 from Nordmann & Rassmann.

Further advantageous oil thickeners for the purposes of the present invention are:
  ozokerite [CAS No. 8021-55-4] and ceresine (paraffin wax, CAS No.: 8001-75-0)
  X-ray amorphous silicon dioxide [CAS No. 7631-86-9] (e.g. Aerosil® 972, Aerosil® 380, Aerosil® R 812),
  hydroxyalkylated guar gum (e.g. hydroxypropylguar gum (Jaguar® HP-8 from Meyhall))
  alkylated guar galactomannans, or ethyl galactomannans (e.g. N-Hance® AG 200 or N-Hance® AG 50 from Hercules Inc., with a degree of substitution of >2]), The total amount of one or more waxes and/or oil thickeners in the finished cosmetic or dermatological preparations is advantageously chosen from the range from 0.1 to 30.0% by weight, preferably between 0.5 and 15% by weight, based on the total weight of the preparations.

The cosmetic or dermatological photoprotection formulations according to the invention can have the customary composition and be used for cosmetic or dermatological photoprotection, in addition for the treatment, care and cleansing of the skin and/or of the hair and as a make-up product in decorative cosmetics.

Depending on their formulation, cosmetic or topical dermatological compositions for the purposes of the present invention may be used, for example, as skin protection cream, cleansing milk, day or night cream etc. It is in some cases possible and advantageous to use the compositions according to the invention as a basis for pharmaceutical formulations.

For use, the cosmetic and dermatological preparations are applied to the skin and/or the hair in a sufficient amount in the manner customary for cosmetics.

The cosmetic and dermatological preparations according to the invention can comprise cosmetic auxiliaries as are customarily used in such preparations, e.g. preservatives, preservation helpers, bactericides, perfumes, substances to prevent foaming, dyes, pigments which have a coloring action, thickeners, moisturizing and/or humectant substances, fillers which improve the feel of the skin, fats, oils, waxes or other customary constituents of a cosmetic or dermatological formulation, such as alcohols, polyols, polymers, foam stabilizers, electrolytes, organic solvents or silicone derivatives.

Advantageous preservatives for the purposes of the present invention are, for example, formaldehyde donors (such as e.g. DMDM hydantoin, which is available, for example, under the trade name Glydant™ from Lonza), iodopropyl butylcarbamates (e.g. those available under the trade names Glycacil-L, Glycacil-S from Lonza, and/or Dekaben LMB from Jan Dekker), parabens (i.e. p-hydroxybenzoic alkyl esters, such as methyl, ethyl-, propyl- and/or butylparaben), phenoxyethanol, ethanol, benzoic acid and the like. According to the invention, the preservative system usually also advantageously includes preservation helpers, such as, for example, octoxyglycerol, glycine soya etc. as well.

Particularly advantageous preparations are also obtained when antioxidants are used as additives or active ingredients. According to the invention, the preparations advantageously comprise one or more antioxidants. Favorable, but nevertheless optional antioxidants which may be used are all antioxidants customary or suitable for cosmetic and/or dermatological applications.

For the purposes of the present invention, it may be particularly advantageous to use water-soluble antioxidants, such as, for example, vitamins, e.g. ascorbic acid and derivatives thereof, and D-biotin, natural and/or synthetic isoflavonoids, alpha-glucosylrutin, panthenol, aloe vera.

The amount of antioxidants (one or more compounds) in the preparations is preferably 0.001 to 30% by weight, particularly preferably 0.05 to 20% by weight, in particular 0.1 to 10% by weight, based on the total weight of the preparation.

It is particularly advantageous when the cosmetic preparations according to the present invention comprise cosmetic or dermatological active ingredients, preferred active ingredients being antioxidants which can protect the skin against oxidative stress.

Advantageous further active ingredients are natural active ingredients and/or derivatives thereof, such as e.g. phytoene, carnitine, carnosine, creatine, taurine and/or β-alanine.

Formulations according to the invention, which comprise e.g. known antiwrinkle active ingredients, such as flavone glycosides (in particular α-glycosylrutin), coenzyme Q10, vitamin E and/or derivatives and the like, are particularly advantageously suitable for the prophylaxis and treatment of cosmetic or dermatological changes in skin, as arise, for example, during skin aging (such as, for example, dryness, roughness and formation of dryness wrinkles, itching, reduced refatting (e.g. after washing), visible vascular dilations (teleangiectases, couperosis), flaccidity and formation of wrinkles and lines, local hyperpigmentation, hypopigmentation and abnormal pigmentation (e.g. age spots), increased susceptability to mechanical stress (e.g. cracking) and the like). In addition, they are advantageously suitable against the appearance of dry or rough skin.

The water phase of the preparations according to the invention can advantageously comprise customary cosmetic auxiliaries, such as, for example, alcohols, in particular those of low carbon number, preferably ethanol and/or isopropanol, diols or polyols of low carbon number, and ethers thereof, preferably propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, polymers, foam stabilizers, electrolytes, and in particular one or more thickeners which may advantageously be chosen from the group consisting of silicon dioxide, aluminum silicates, polysaccharides or derivatives thereof, e.g. hyaluronic acid, xanthan gum, hydroxypropylmethylcellulose, particularly advantageously from the group of polyacrylates, preferably a polyacrylate from the group of so-called carbopols, for example Carbopol 980, 981, 1382, 2984, 5984, in each case individually or in combination.

Also advantageous are copolymers of $C_{10-30}$-alkyl acrylates and one or more monomers of acrylic acid, of methacrylic acid or esters thereof which are crosslinked with an allyl ether of sucrose or an allyl ether of pentaerythritol.

Compounds which bear the INCI name "Acrylates/$C_{10-30}$ Alkyl Acrylate Crosspolymer" are advantageous. Those available under the trade names Pemulen TR1 and Pemulen TR2 from B. F. Goodrich Company are particularly advantageous.

Compounds which bear the INCI name Ammonium Acryloyidimethyltaurate/Vinylpyrrolidone copolymers are advantageous.

According to the invention, the Ammonium Acryloyldimethyltaurate/Vinylpyrrolidone copolymers advantageously have the empirical formula $[C_7H_{16}N_2SO_4]_n \; [C_6H_9NO]_m$, corresponding to a statistical structure as follows

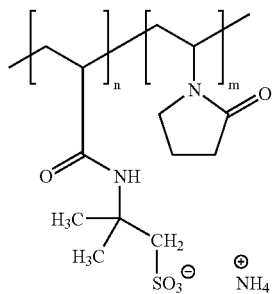

Preferred species for the purposes of the present invention are listed in Chemical Abstracts under the Registry numbers 58374-69-9, 13162-05-5 and 88-12-0 and are available under the trade name Aristoflex® AVC from Clariant GmbH.

Also advantageous are copolymers/crosspolymers comprising Acryloyidimethyl Taurate, such as, for example, Simugel® EG from Seppic S.A.

Moisturizers can also preferably be used.

Moisturizers is the term used for substances or mixtures of substances which, following application or distribution on the surface of the skin, confer on cosmetic or dermatological preparations the property of reducing the moisture loss by the horny layer (also called transepidermal water loss (TEWL)) and/or have a positive influence on the hydration of the horny layer.

Advantageous moisturizers for the purposes of the present invention are, for example, glycerol, lactic acid and/or lactates, in particular sodium lactate, butylene glycol, propylene glycol, biosaccaride gum-1, glycine soya, ethylhexyloxyglycerol, pyrrolidonecarboxylic acid and urea. In addition, it is particularly advantageous to use polymeric moisturizers from the group of water-soluble and/or water-swellable and/or water-gellable polysaccharides. Particularly advantageous are, for example, hyaluronic acid, chitosan and/or a fucose rich polysaccharide which is listed in Chemical Abstracts under the Registry number 178463-23-5 and is available, for example, under the name Fucogel® 1000 from SOLABIA S.A.

The cosmetic or dermatological preparations according to the invention can also advantageously, but not necessarily, comprise fillers which, for example, further improve the sensory and cosmetic properties of the formulations and, for example, bring about or intensify a velvety or silky feel on the skin. Advantageous fillers for the purposes of the present invention are starch and starch derivatives (such as tapioca starch, distarch phosphate, aluminum or sodium starch octenylsuccinate and the like), pigments which primarily have neither a UV filter effect nor a coloring effect (such as e.g. boron nitride etc.) and/or Aerosils® (CAS No. 7631-86-9).

The oil phase of the formulations according to the invention is advantageously chosen from the group of polar oils, for example from the group of lecithins and of fatty acid triglycerides, namely the triglycerol esters of saturated and/or unsaturated, branched and/or unbranched alkanecarboxylic acids with a chain length from 8 to 24, in particular 12 to 18, carbon atoms. The fatty acid triglycerides can, for example, advantageously be chosen from the group of synthetic, semisynthetic and natural oils, such as e.g. cocoglyceride, olive oil, sunflower oil, soybean oil, peanut oil, rapeseed oil, almond oil, palm oil, coconut oil, castor oil, wheatgerm oil, grapeseed oil, thistle oil, evening primrose oil, macadamia nut oil and the like.

Also advantageous according to the invention are e.g. natural waxes of animal and vegetable origin, such as, for example beeswax and other insect waxes, and berry wax, shea butter and/or lanolin (wool wax).

Further advantageous polar oil components for the purposes of the present invention may also be chosen from the group of esters of saturated and/or unsaturated, branched and/or unbranched alkanecarboxylic acids with a chain length of from 3 to 30 carbon atoms and saturated and/or unsaturated, branched and/or unbranched alcohols with a chain length of from 3 to 30 carbon atoms, and from the group of esters of aromatic carboxylic acids and saturated and/or unsaturated, branched and/or unbranched alcohols with a chain length from 3 to 30 carbon atoms. Such ester oils can then advantageously be chosen from the group consisting of octyl palmitate, octyl cocoate, octyl isostearate, octyldodeceyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as e.g. jojoba oil.

The oil phase can also advantageously be chosen from the group of dialkyl ethers and dialkyl carbonates, advantageous examples being dicaprylyl ether (Cetiol OE) and/or dicaprylyl carbonate, for example that available under the trade name Cetiol CC from Cognis.

It is also preferred to choose the oil component(s) from the group consisting of isoeicosane, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethylisosorbide. It is particularly advantageous if the oil phase of the formulations according to the invention has a content of $C_{12-15}$-alkyl benzoate or consists entirely of this.

Advantageous oil components are also e.g. butyloctyl salicylate (for example that available under the trade name Hallbrite BHB from CP Hall), hexadecyl benzoate and butyloctyl benzoate and mixtures thereof (Hallstar AB).

Any desired mixtures of such oil and wax components can be used advantageously for the purposes of the present invention.

In addition, the oil phase can likewise advantageously also comprise nonpolar oils, for example those chosen from the group of branched and unbranched hydrocarbons and hydrocarbon waxes, in particular mineral oil, vaseline (petrolatum), paraffin oil, squalane and squalene, polyolefins, hydrogenated polyisobutenes and isohexadecane. Among the polyolefins, polydecenes are the preferred substances.

The oil phase can also advantageously have a content of cyclic or linear silicone oils or consist entirely of such oils, although it is preferred to use an additional content of other oil phase components apart from the silicone oil or the silicone oils.

Silicone oils are high molecular weight synthetic polymeric compounds in which silicon atoms are linked in a chain-like and/or network-like manner via oxygen atoms, and the remaining valences of the silicon are saturated by hydrocarbon radicals (in most cases methyl, less often ethyl, propyl, phenyl groups etc.). Systematically, the silicone oils are referred to as polyorganosiloxanes. The methyl-substituted polyorganosiloxanes, which represent the most significant compounds of this group in terms of number and are characterized by the following structural formula

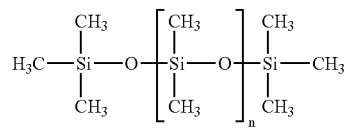

are also referred to as polydimethylsiloxane or Dimethicone (INCI). There are dimethicones with various chain lengths and with various molecular weights.

For the purposes of the present invention, particularly advantageous polyorganosiloxanes are, for example, dimethylpolysiloxanes [poly(dimethylsiloxane)], which are available, for example, under the trade names Abil 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane or decamethylcyclopentasiloxane), which are also referred to as Cyclomethicones in accordance with INCI, amino-modified silicones (INCI: Amodimethicone) and silicone waxes, e.g. polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are available as various Abil wax grades from Th. Goldschmidt. However, for the purposes of the present invention, other silicone oils can also advantageously be used, for example cetyldimethicone, hexamethylcyclotrisiloxane, polydimethylsiloxane, poly(methylphenylsiloxane).

For the purposes of the present invention, it is also advantageous to create cosmetic and dermatological preparations whose main purpose is not protection against sunlight, but which nevertheless contain a content of further UV protection substances. Thus, for example, UV-A and/or UV-B filter substances are usually incorporated into day creams or make-up products. UV protection substances, like antioxidants and, if desired, preservatives, represent effective protection of the preparations themselves against decay. Also favorable are cosmetic and dermatological preparations which are in the form of a sunscreen composition.

Accordingly, the preparations within the meaning of the present invention preferably comprise at least one further UV-A, UV-B and/or broadband filter substance. The formulations may, but do not necessarily, optionally also comprise one or more organic and/or inorganic pigments as UV filter substances, which may be present in the water phase and/or the oil phase.

In addition, the preparations according to the invention can advantageously also be in the form of so-called oil-free cosmetic or dermatological emulsions, which comprise a water phase and at least one UV filter substance which is liquid at room temperature and/or one or more silicone derivatives as the further phase. Oil-free formulations for the purposes of the present invention may advantageously also comprise further lipophilic components—such as, for example, lipophilic active ingredients.

Particularly advantageous UV filter substances which are liquid at room temperature for the purposes of the present invention are homomenthyl salicylate (INCI: Homosalate), 2-ethylhexyl 2-cyano-3,3-diphenylacrylate (INCI: Octocrylene), 2-ethylhexyl 2-hydroxybenzoate (2-ethylhexyl salicylate, octyl salicylate, INCI: Octyl Salicylate) and esters of cinnamic acid, preferably 4-methoxycinnamic 2-ethylhexyl ester (2-ethylhexyl 4-methoxycinnamate, INCI: Octyl Methoxycinnamate) and 4-methoxycinnamic isopentyl ester (isopentyl 4-methoxycinnamate, INCI: Isoamyl p-Methoxycinnamate).

Preferred inorganic pigments are metal oxides and/or other metal compounds which are sparingly soluble or insoluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides, and the sulfate of barium ($BaSO_4$).

The pigments can advantageously be used for the purposes of the present invention also in the form of commercially available oily or aqueous predispersions. Dispersion auxiliaries and/or solubility promoters may advantageously be added to these predispersions.

The pigments may, according to the invention, advantageously be surface-treated ("coated"), the intention being, for example, to form or retain a hydrophilic, amphiphilic or hydrophobic character. This surface treatment can consist in providing the pigments with a thin hydrophilic and/or hydrophobic inorganic and/or organic layer by methods known per se. The various surface coatings for the purposes of the present invention may also comprise water.

Inorganic surface coatings for the purposes of the present invention may consist of aluminum oxide ($Al_2O_3$), aluminum hydroxide $Al(OH)_3$, or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings may exist on their own, in combination and/or in combination with organic coating materials.

Organic surface coatings for the purposes of the present invention may consist of vegetable or animal aluminum stearate, vegetable or animal stearic acid, lauric acid, dimethylpolysiloxane (also: dimethicone), methylpolysiloxane (methicone), simethicone (a mixture of dimethylpolysiloxane with an average chain length of from 200 to 350 dimethylsiloxane units and silica gel) or alginic acid. These organic surface coatings may exist on their own, in combination and/or in combination with inorganic coating materials.

Zinc oxide particles and predispersions of zinc oxide particles which are suitable according to the invention are available under the following trade names:

| Trade name | Coating | Manufacturer |
| --- | --- | --- |
| Z-Cote HP1 | 2% dimethicone | BASF |
| Z-Cote | / | BASF |
| ZnO NDM | 5% dimethicone | H&R |
| Zinc oxide Neutral | / | H&R |
| MZ 303 M | 5% methicone | Tayca Corp. |

Suitable titanium dioxide particles and predispersions of titanium dioxide particles are available under the following trade names from the companies listed:

| Trade name | Coating | Manufacturer |
| --- | --- | --- |
| MT-100TV | aluminum hydroxide/stearic acid | Tayca Corporation |
| MT-100Z | aluminum hydroxide/stearic acid | Tayca Corporation |
| Eusolex T-2000 | alumina/simethicone | Merck KgaA |
| Titanium dioxide T805 (Uvinul TiO$_2$) | octyltrimethylsilane | Degussa |
| Tioveil AQ 10PG | alumina/silica | Solaveil Uniquema |

Further advantageous pigments are latex particles. Latex particles which are advantageous according to the invention are those described in the following specifications: U.S. Pat. No. 5,663,213 and EP 0 761 201. Particularly advantageous latex particles are those which are formed from water and styrene/acrylate copolymers and are available, for example, under the trade name "Alliance SunSphere" from Rohm & Haas.

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

Advantageous further UV filter substances for the purposes of the present invention are sulfonated, water-soluble UV filters, such as, for example, phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic bis-sodium salt with the INCI name Bisimidazylate (CAS No.: 180898-37-7), which is available, for example, under the trade name Neo Heliopan AP from Haarmann & Reimer;

salts of 2-phenylbenzimidazole-5-sulfonic acid, such as its sodium, potassium or its triethanolammonium salt, and the sulfonic acid itself with the INCI name Phenylbenzimidazole Sulfonic Acid (CAS No. 27503-81-7), which is available, for example, under the trade name Eusolex 232 from Merck or under Neo Heliopan Hydro from Haarmann & Reimer;

1,4-di(2-oxo-10-sulfo-3-bornylidenemethyl)benzene (also: 3,3'-(1,4-phenylene-dimethylene)bis(7,7-dimethyl-2-oxobicyclo[2.2.1]hept-1-ylmethane sulfonic acid) and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di(2-oxo-3-bornylidenemethyl-10-sulfonic acid) has the INCI name Terephthalidene Dicamphor Sulfonic Acid (CAS No.: 90457-82-2) and is available, for example, under the trade name Mexoryl SX from Chimex;

sulfonic acid derivatives 3-benzylidenecamphor, such as e.g. 4-(2-oxo-3-bornylidenemethyl)benzenesulfonic acid, 2-methyl-5-(2-oxo-3-bornylidenemethyl)sulfonic acid and salts thereof.

Advantageous UV filter substances for the purposes of the present invention are also so-called broadband filters, i.e. filter substances which absorb both UV-A- and also UV-B-radiation.

Advantageous broadband filters or UV-B filter substances are, for example, triazine derivatives, such as e.g.

2,4-bis{[4-(2-ethylhexyloxy)-2-hydroxylphenyl]-6-(4-methoxyphenyl)-1,3,5-triazine (INCI: Methylene Bis-Benzotriazolemethylbutylphenol), which is available under the trade name Tinosorb® S from CIBA-Chemikalien GmbH;

dioctylbutylamidotriazone (INCI: Diethylhexylbutamidotriazone), which is available under the trade name UVASORB HEB from Sigma 3V;

tris (2-ethylhexyl)4,4',4"-(1,3,5-triazine-2,4,6-triyltriimino)trisbenzoate, also: 2,4,6-tris[anilino(p-carbo-2'-ethyl-1'-hexyloxy)]-1,3,5-triazine (INCI: Octyl Triazone), which is sold by BASF Aktiengesellschaft under the trade name UVINUL® T 150.

An advantageous broadband filter for the purposes of the present invention is also 2,2'-methylenebis(6-(2H-benzotriazol-2-yl)-4-(1,1,3,3-tetramethylbutyl)phenol) (INCI: Bisoctyltriazole), which is available under the trade name Tinosorb® M from CIBA-Chemikalien GmbH.

An advantageous broadband filter for the purposes of the present invention is also 2-(2H-benzotriazol-2-yl)-4-methyl-6-[2-methyl-3-[1,3,3,3-tetramethyl-1-[(trimethylsilyl)oxy]disiloxanyl]propyl]phenol (CAS No.: 155633-54-8) with the INCI name Drometrizole Trisiloxane, which is available under the trade name Mexoryl® XL from Chimex.

The further UV filter substances may be oil-soluble. Advantageous oil-soluble filter substances are e.g.:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate amyl 4-(dimethylamino) benzoate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bound to polymers.

A further photoprotective filter substance to be used advantageously according to the invention is ethylhexyl 2-cyano-3,3-diphenyl acrylate (Octocrylene), which is available from BASF under the name Uvinul® N 539.

Particularly advantageous preparations for the purposes of the present invention, which may be characterized by a high or very high UV-A protection, comprise, as well as the filter substance(s) according to the invention, preferably also further UV-A and/or broadband filters, in particular dibenzoylmethane derivatives [for example 4-(tert-butyl)-4'-methoxydibenzoylmethane] and/or 2,4-bis{[4-(2-ethylhexyloxy)-2-hydroxy]phenyl}-6-(4-methoxyphenyl)-1,3,5-triazine, in each case individually or in any combinations with one another.

The list of UV filters specified which can be used for the purposes of the present invention is not of course intended to be limiting.

Advantageously, the preparations according to the invention comprise the substances which absorb UV radiation in the UV-A and/or UV-B region in a total amount of e.g. 0.1% by weight to 30% by weight, preferably 0.5 to 20% by weight, in particular 1.0 to 15.0% by weight, in each case based on the total weight of the preparations, in order to provide cosmetic preparations which protect the hair and/or the skin from the entire range of ultraviolet radiation.

In addition, it may in some instances be advantageous to incorporate film formers into the cosmetic or dermatological preparations according to the invention, for example in order to improve the water resistance of the preparations or to increase the UV protection performance (UV-A and/or UV-B boosting). Water-soluble or dispersible and also fat-soluble film formers are suitable, in each case individually or in combination with one another.

Advantageous water-soluble or dispersible film formers are e.g. polyurethanes (e.g the Avalure® grades from Goodrich), Dimethicone Copolyol Polyacrylate (Silsoft Surface® from Witco Organo Silicones Group), PVP/VA (VA=vinyl acetate) copolymer (Luviscol VA 64 Powder from BASF) etc.

Advantageous fat-soluble film formers are e.g. the film formers from the group of polymers based on polyvinylpyrrolidone (PVP)

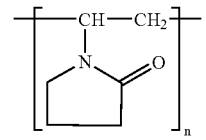

Particular preference is given to copolymers of polyvinylpyrrolidone, for example the PVP hexadecene copolymer and the PVP eicosene copolymer, which are available under the trade names Antaron V216 and Antaron V220 from GAF Chemicals Cooperation and also tricontayl PVP and the like.

The examples below serve to illustrate the present invention without limiting it. The numerical values in the examples are percentages by weight, based on the total weight of the particular preparations.

EXAMPLES

1. O/W Sunscreen Emulsions

|  | 1 | 2 | 3 | 4 | 5 | 6 | 7 |
|---|---|---|---|---|---|---|---|
| Glycerol monostearate SE | 0.50 | 1.00 | 3.00 |  |  | 1.50 |  |
| Glyceryl stearate citrate | 2.00 |  |  | 1.00 | 2.00 |  | 2.50 |
| Stearic acid |  | 3.00 |  | 2.00 |  |  |  |
| PEG-40 stearate | 0.50 |  |  |  |  | 2.00 |  |
| PEG-100 stearate |  |  |  | 4.50 |  | 1.50 | 0.75 |
| Stearyl alcohol |  |  | 3.00 |  |  | 2.00 | 0.50 |
| Cetyl alcohol | 2.50 | 1.00 |  | 1.50 | 0.50 |  | 2.00 |
| Ethylhexyl methoxycinnamate |  |  |  | 5.00 | 6.00 |  | 8.00 |
| Anisotriazine |  |  | 3.00 | 2.00 |  |  | 2.50 |
| Butylmethoxydibenzoylmethane |  |  |  | 1.50 | 2.80 | 2.00 | 1.50 |
| Bisimidazylate | 2.50 |  |  |  | 1.00 |  | 0.30 |
| Ethylhexyltriazone | 4.00 |  | 3.00 | 4.00 | 4.00 | 2.00 |  |
| 4-Methylbenzylidenecamphor | 4.00 |  |  |  | 2.00 | 4.00 | 2.00 |
| Octocrylene |  |  | 7.50 |  |  |  | 2.50 |
| Diethylhexylbutamidotriazone | 1.00 |  | 1.00 |  | 1.00 |  |  |
| Phenylbenzimidazolesulfonic acid | 0.50 |  |  | 3.00 |  |  |  |
| Bisoctyltriazole | 2.00 |  | 0.50 | 1.50 | 2.50 |  |  |
| Homosalate |  |  |  |  |  |  |  |
| Ethylhexylsalicylate |  |  | 3.00 |  |  |  | 5.00 |
| Drometrizole trisiloxane |  |  | 0.5 |  |  | 1.00 |  |
| Terephthalidenedicamphor-sulfonic acid |  |  |  |  | 1.00 | 0.50 |  |
| Diethylhexyl-2,6-naphthalate | 3.50 | 4.80 | 7.00 | 9.50 | 6.70 | 5.50 | 8.00 |
| Titanium dioxide MT-100Z | 1.00 |  |  |  | 2.00 | 2.00 |  |
| Zinc oxide HP1 |  |  | 1.50 | 1.00 |  | 2.00 | 3.00 |
| C12–15 alkylbenzoate |  | 2.50 |  |  | 4.00 | 7.00 | 5.00 |
| Dicaprylyl ether |  |  |  | 3.50 |  | 2.00 |  |
| Butylene glycol dicaprylate/Dicaprate | 5.00 |  |  | 6.00 |  |  |  |

-continued

|  | 1 | 2 | 3 | 4 | 5 | 6 | 7 |
|---|---|---|---|---|---|---|---|
| Dicaprylyl carbonate |  |  |  | 6.00 |  | 2.00 | 2.00 |
| Dimethicone |  | 0.50 | 1.00 |  | 2.00 |  |  |
| Cyclomethicone | 2.00 |  |  | 0.50 |  |  | 0.50 |
| Ethylgalactomannan (N-Hance ® AG200) |  | 3.50 |  | 2.00 |  |  | 1.00 |
| C$_{18-36}$ Triglyceride | 2.00 |  | 5.50 | 3.00 |  |  |  |
| Hydrogenated cocoglyceride |  |  |  |  | 4.50 | 3.00 | 2.00 |
| Shea butter |  | 2.00 |  |  |  |  | 0.50 |
| PVP hexadecene copolymer | 0.50 |  |  | 0.50 | 1.00 |  | 1.00 |
| Tricontanyl PVP |  | 0.50 | 1.00 |  |  |  | 1.00 |
| Glycerol | 3.00 | 7.50 |  | 7.50 | 5.00 |  | 2.50 |
| Xanthan gum | 0.15 |  | 0.05 |  |  |  | 0.30 |
| Sodium carbomer |  | 0.20 | 0.10 | 0.20 |  |  |  |
| Vitamin E |  | 0.50 | 1.00 |  |  |  | 0.25 |
| Alpha-glucosylrutin |  |  | 0.10 | 0.45 | 0.12 | 0.30 | 0.10 |
| Vitamin A | 0.50 |  |  |  | 0.75 |  | 1.00 |
| DMDM hydantoin |  | 0.60 | 0.40 | 0.20 |  |  |  |
| Konkaben LMB ® |  |  |  | 0.18 | 0.20 | 0.10 | 0.15 |
| Methylparaben | 0.15 |  | 0.25 |  | 0.50 |  |  |
| Phenoxyethanol | 1.00 | 0.40 |  | 0.40 | 0.50 | 0.40 | 0.60 |
| Ethanol |  | 2.00 | 1.50 |  | 3.00 |  | 1.00 |
| Perfume | 0.20 | 0.20 | 0.20 | 0.20 | 0.20 | 0.20 | 0.20 |
| Water | ad 100 | ad 100 | ad 100 | ad 100 | ad 100 | ad 100 | ad 100 |

2. Hydrodispersions

|  | 1 | 2 | 3 | 4 | 5 |
|---|---|---|---|---|---|
| Ceteareth-20 | 1.00 |  |  | 0.5 |  |
| Cetyl alcohol |  |  | 1.00 |  |  |
| Sodium carbomer |  | 0.20 |  | 0.30 |  |
| Acrylates/C10–30 alkyl acrylate crosspolymer | 0.50 |  | 0.40 | 0.10 | 0.10 |
| Xanthan gum |  | 0.30 | 0.15 |  | 0.50 |
| Ethylhexyl methoxycinnamate |  |  |  | 5.00 |  |
| Anisotriazine |  | 1.50 |  | 2.00 |  |
| Butylmethoxydibenzoyl-methane | 1.00 | 0.50 |  | 3.00 |  |
| Bisimidazole | 0.50 |  |  | 2.00 |  |
| Ethylhexyltriazone | 4.00 |  | 3.00 | 4.00 |  |
| Octocrylene |  | 4.00 | 3.90 |  |  |
| Diethylhexylbutamido-triazone | 1.00 |  |  | 2.00 |  |
| Phenylbenzimidazole-sulfonic acid | 0.50 |  |  | 3.00 |  |
| Bisoctyltriazole | 2.50 | 0.50 |  |  |  |
| Drometrizole trisiloxane |  |  | 1.00 |  |  |
| Diethylhexyl 2,6-naphthalate | 4.50 | 8.00 | 7.20 | 5.50 | 14.00 |
| Titanium dioxide MT-100Z | 0.50 |  | 2.00 |  |  |
| Zinc oxide HP1 |  |  | 1.00 | 2.00 |  |
| C$_{18-36}$ triglyceride | 3.50 | 2.50 |  |  |  |
| Glyceryl tri(12-hydroxystearate) |  |  | 4.00 |  |  |
| Shea butter |  |  | 2.50 | 4.50 |  |
| C12–15 alkyl benzoate | 2.00 | 2.50 |  |  |  |
| Cocoglycerides (Myritol ® 331) |  | 4.00 |  |  |  |
| Butylene glycol dicaprylate/dicaprate | 4.00 |  | 2.00 | 6.00 |  |
| Dicaprylyl carbonate |  | 2.00 | 6.00 |  |  |
| Dimethicone |  | 0.50 | 1.00 |  |  |
| Phenyltrimethicone | 2.00 |  |  | 0.50 | 2.00 |
| PVP hexadecene copolymer | 0.50 |  |  | 0.50 | 1.00 |
| Tricontanyl PVP | 0.50 |  | 1.00 |  |  |
| Ethylhexylglycerol |  |  | 1.00 |  | 0.50 |
| Glycerol | 3.00 | 7.50 |  | 7.50 | 2.50 |
| Glycine soya |  |  | 1.50 |  |  |
| Vitamin E | 0.50 |  | 0.25 |  | 1.00 |
| Alpha-glucosylrutin |  |  | 0.35 | 0.50 |  |
| DMDM hydantoin |  | 0.60 | 0.40 | 0.20 |  |
| Konkaben LMB ® | 0.20 |  |  |  | 0.15 |
| Methylparaben | 0.50 |  | 0.25 | 0.15 |  |
| Phenoxyethanol | 0.50 | 0.40 |  | 1.00 | 0.60 |
| Fucogel ®-1000 |  |  |  |  |  |
| Ethanol | 3.00 | 2.00 | 1.50 |  | 1.00 |
| Dyes, water-soluble |  |  |  | 0.12 |  |
| Perfume | 0.20 | 0.20 | 0.20 | 0.20 | 0.20 |
| Water | ad 100 | ad 100 | ad 100 | ad 100 | ad 100 |

3. W/O Sunscreen Emulsions

|  | 1 | 2 | 3 | 4 | 5 |
|---|---|---|---|---|---|
| Cetyldimethicone copolyol |  | 2.50 |  | 4.00 |  |
| Laurylmethicone copolyol |  |  | 1.50 |  |  |
| Polyglyceryl-2 dipolyhydroxystearate | 5.00 |  |  |  | 4.50 |
| PEG-30 dipolyhydroxystearate |  |  | 5.00 |  |  |
| Ethylhexyl methoxycinnamate |  | 8.00 |  | 5.00 | 4.00 |
| Anisotriazine | 2.00 | 2.50 |  | 2.00 | 2.50 |
| Butylmethoxydibenzoyl-methane |  | 3.00 | 2.00 | 1.00 |  |
| Bisimidazylate |  |  |  | 2.00 | 3.00 |
| Ethylhexyltriazone |  |  | 3.00 | 4.00 |  |
| Octocrylene | 0.90 | 2.50 | 3.90 |  | 2.50 |
| Diethyhexylbutamido-triazone | 1.00 |  |  | 2.00 |  |
| Phenylbenzimidazole-sulfonic acid | 0.50 |  |  | 3.00 | 2.00 |
| Bisoctyltriazole |  |  | 2.00 | 0.50 |  |
| Drometrizole trisiloxane |  | 1.00 | 0.25 | 2.00 |  |
| Terephthalidenedi-camphorsulfonic acid |  |  |  | 1.00 |  |

-continued

|  | 1 | 2 | 3 | 4 | 5 |
|---|---|---|---|---|---|
| Diethylhexyl 2,6-naphthalate | 8.00 | 3.50 | 10.00 | 8.50 | 12.00 |
| Titanium dioxide T805 |  | 2.00 | 1.50 |  | 3.00 |
| Z-Cote ®HP1 | 1.00 |  | 3.00 |  | 7.00 |
| Mineral oil |  |  | 10.0 |  | 8.00 |
| C12–15 alkyl benzoate |  |  |  | 9.00 |  |
| Dicaprylyl ether | 10.00 |  |  |  | 7.00 |
| Butylene glycol dicaprylate/Dicaprate |  | 2.00 |  | 8.00 | 4.00 |
| Dicaprylyl carbonate | 5.00 |  | 6.00 |  |  |
| Dimethicone |  | 4.00 | 1.00 | 5.00 |  |
| Cyclomethicone | 2.00 | 25.00 |  |  | 2.00 |
| Shea butter |  |  | 3.00 |  |  |
| Bentone ® 38 | 4.00 |  |  |  |  |
| Glyceryl tribehenate |  | 3.50 |  | 2.50 |  |
| Siliconyl beeswax |  | 1.25 |  |  | 6.00 |
| Carnauba wax | 3.00 |  |  |  |  |
| Ethylgalactomannan |  |  | 3.50 | 5.00 |  |
| PVP hexadecene copolymer | 0.50 |  |  | 0.50 | 1.00 |
| Tricontanyl PVP |  |  | 0.50 | 1.00 | 0.50 |
| Ethylhexylglycerol |  | 0.30 | 1.00 |  | 0.50 |
| Glycerol | 3.00 | 7.50 |  | 7.50 | 2.50 |
| Glycine soya |  | 1.00 | 1.50 |  |  |
| MgSO4 | 1.00 | 0.50 |  |  |  |
| Vitamin E acetate | 0.50 |  | 0.25 |  | 1.00 |
| DMDM hydantoin |  | 0.60 | 0.40 | 0.20 |  |
| Methylparaben | 0.50 |  | 0.25 | 0.15 |  |
| Phenoxyethanol | 0.50 | 0.40 |  | 1.00 | 0.60 |
| Ethanol | 3.00 |  | 1.50 |  | 1.00 |
| Perfume | 0.20 | 0.20 | 0.20 | 0.20 | 0.20 |
| Water | ad 100 | ad 100 | ad 100 | ad 100 | ad 100 |

4. Solids-Stabilized Emulsions

|  | 1 | 2 | 3 | 4 | 5 |
|---|---|---|---|---|---|
| Mineral oil |  |  |  |  | 16.0 |
| Octyldodecanol | 6.0 |  | 7.5 | 7.5 | 5.0 |
| Caprylic/capric triglyceride |  |  |  |  | 6.0 |
| C12–15-alkyl benzoate | 7.0 | 8.0 | 7.5 | 7.5 |  |
| Butylene glycol dicaprylate/Dicaprate | 4.0 | 8.0 |  |  |  |
| Dicaprylyl ether |  | 8.0 | 7.5 | 7.5 |  |
| Dicaprylyl carbonate | 4.0 |  |  |  |  |
| Hydroxyoctacosanyl hydroxystearate | 2.0 |  | 2.0 | 2.0 | 1.5 |
| PVP/hexadecene copolymer |  |  |  | 1.0 | 0.7 |
| Disteardimonium hectorite | 1.0 | 1.0 |  | 0.5 | 1.0 |
| Dimethicone |  | 2.0 |  |  |  |
| Cyclomethicone |  |  |  | 2.0 |  |
| Ethylhexyl methoxycinnamate | 5.0 |  | 5.0 |  |  |
| Butylmethoxydibenzoyl-methane | 3.00 | 2.0 | 0.50 | 1.80 | 1.0 |
| 4-Methylbenzylidene-camphor |  | 4.0 |  |  | 2.0 |
| Ethylhexyltriazone | 2.0 | 2.0 |  |  | 1.0 |
| Bisoctyltriazole |  | 3.00 |  | 2.50 |  |
| Anisotriazine | 2.5 |  | 2.5 |  |  |
| Eusolex T-2000 | 1.5 | 4.0 | 0.5 |  | 1.5 |
| Titanium dioxide T 805 |  |  |  | 2.0 |  |
| Zinc oxide NDM |  | 4.5 | 2.0 |  |  |
| Phenylbenzimidazole-sulfonic acid | 2.0 |  |  |  |  |
| Bisimidazylate |  | 1.00 |  | 1.50 | 3.00 |
| Boron nitride |  |  |  |  | 0.5 |
| C18–36 triglyceride |  |  | 4.5 |  | 1.5 |

-continued

|  | 1 | 2 | 3 | 4 | 5 |
|---|---|---|---|---|---|
| Hydrogenated cocoglyceride |  | 2.5 |  |  |  |
| C20–40 alkyl stearate | 3.5 |  |  | 5.0 |  |
| Starch/sodium metaphosphate polymer | 0.5 |  | 1.5 |  |  |
| Corn starch modified |  |  | 1.0 |  |  |
| Acrylate copolymer |  |  |  | 0.25 |  |
| Talc |  |  |  | 2.0 |  |
| Sodium chloride | 1.0 | 1.0 | 1.0 |  |  |
| Diethylhexyl 2,6-naphthalate | 4.00 | 6.50 | 7.50 | 9.50 | 5.00 |
| Polyurethane |  | 0.50 | 1.50 |  | 0.40 |
| Magnesium sulfate |  |  |  |  | 0.70 |
| Sodium hydroxide solution 45% | 0.5 | 0.5 |  |  |  |
| Glycerol | 5.0 | 7.5 | 5.0 | 10.0 | 3.0 |
| Trisodium EDTA |  | 1.0 | 1.0 |  | 1.0 |
| Propylene carbonate | 0.33 | 0.33 | 0.33 |  | 0.33 |
| Methylparaben | 0.21 | 0.21 | 0.2 | 0.2 | 0.21 |
| Propylparaben | 0.07 | 0.07 |  |  | 0.07 |
| Phenoxyethanol | 0.5 | 0.5 | 0.5 | 0.5 | 0.5 |
| Hexamidine diisethionate |  |  |  | 0.08 | 0.08 |
| Alcohol |  | 5.0 |  |  |  |
| Perfume | 0.15 |  |  | 0.50 | 0.35 |
| Water | ad 100 | ad 100 | ad 100 | ad 100 | ad 100 |

5. Sticks

|  | 1 | 2 | 3 | 4 |
|---|---|---|---|---|
| Caprylic/capric triglyceride | 12 | 10 | 6 |  |
| Octyldodecanol | 7 | 14 | 8 | 3 |
| Butylene glycol dicaprylate/dicaprate |  |  |  | 12 |
| Pentaerythrityl tetraisostearate | 10 | 6 | 8 | 7 |
| Polyglyceryl-3 diisostearate | 2.5 |  |  |  |
| Bis-diglyceryl polyacyladipate-2 | 9 | 8 | 10 | 8 |
| Cetearyl alcohol | 8 | 11 | 9 | 7 |
| Myristyl myristate | 3.5 | 3 | 4 | 3 |
| Beeswax | 5 | 5 | 6 | 6 |
| Cera carnauba | 1.5 | 2 | 2 | 1.5 |
| Cera alba | 0.5 | 0.5 | 0.5 | 0.5 |
| C16–40 alkyl stearate |  | 1.5 | 1.5 | 1.5 |
| Diethylhexyl 2,6-naphthalate | 5.5 | 13.0 | 2.5 | 8.0 |
| Butylmethoxydibenzoylmethane |  | 1 | 1 |  |
| Z-Cote ® HP1 |  |  |  | 4.5 |
| MT-100 TV |  | 4 | 2.5 |  |
| 4-Methylbenzylidenecamphor |  | 3.6 |  | 5 |
| Ethylhexyl methoxycinnamate | 3 | 3.6 | 7.5 | 2.5 |
| Anisotriazine | 2.5 |  |  | 5 |
| Octocrylene |  |  | 7.5 |  |
| Benzophenone-3 |  |  | 3.5 |  |
| Ethylhexyltriazone | 2 |  |  |  |
| Diethylhexylbutamidotriazone |  |  |  | 3 |
| Tocopheryl acetate | 0.5 | 1 | 1 | 1 |
| Tocopherol; ascorbyl palmitate | 0.05 | 0.05 | 0.05 | 0.05 |
| Buxus chinensis | 2 | 1 | 1 | 1 |
| Perfume, BHT | q.s | q.s | q.s | q.s |
| Ricinus communis | ad 100 | ad 100 | ad 100 | ad 100 |

|  | 1 | 2 | 3 | 4 | 5 | 6 | 7 | 8 |
|---|---|---|---|---|---|---|---|---|
| Glycerol monostearate SE | 0.50 | 2.00 | 3.00 | 5.00 |  |  | 0.50 | 4.00 |
| Glyceryl isostearate |  |  |  |  | 3.50 | 4.00 | 2.00 |  |
| Isoceteth-20 |  | 0.50 |  |  | 2.00 |  |  |  |
| Ceteareth-12 |  | 5.00 |  | 1.00 |  |  |  | 3.50 |
| Ceteareth-20 |  |  |  | 2.00 |  | 2.50 | 3.00 |  |
| PEG-100 stearate | 5.00 |  | 1.00 |  | 1.00 |  |  | 0.50 |
| Cetyl alcohol | 2.50 | 1.00 |  | 1.50 |  | 0.50 | 1.50 |  |
| Cetyl palmitate |  |  |  | 0.50 |  | 1.00 |  |  |
| Cetyl dimethicone copolyol | 0.50 |  |  |  | 0.50 |  | 1.00 |  |
| Polyglyceryl-2 dipolyhydroxystearate |  |  | 0.75 | 0.25 |  |  |  |  |
| Diethylhexyl 2,6-naphthalate | 7.0 | 3.5 | 8.00 | 6.0 | 15.0 | 4.0 | 5.0 | 4.5 |
| Anisotriazine |  |  | 0.50 | 2.00 |  | 3.00 |  |  |
| Butylmethoxydibenzoylmethane | 1.50 |  | 1.00 |  | 5.00 | 1.00 | 0.75 |  |
| Bisimidazylate |  | 2.00 |  |  | 1.00 |  |  |  |
| Terephthalidenedicamphor-sulfonic acid |  |  | 0.50 |  |  |  | 1.00 |  |
| Drometrizole trisiloxane |  |  | 2.00 |  |  | 3.00 |  | 1.00 |
| Ethylhexyl methoxycinnamate | 8.00 |  |  | 4.50 | 5.00 | 8.00 |  |  |
| Ethylhexyl salicylate | 4.00 |  |  |  | 3.50 | 4.00 |  |  |
| Dioctylbutamidotriazone |  |  |  | 3.00 | 2.00 | 2.00 |  | 1.50 |
| Ethylhexyltriazone |  |  | 2.00 | 4.00 |  |  | 1.50 | 3.00 |
| Dimethicone diethylbenzalmalonate |  | 4.50 |  |  | 3.50 |  |  |  |
| Octocrylene |  |  | 5.00 |  | 8.00 |  |  | 7.50 |
| Phenylbenzimidazolesulfonic acid | 1.00 | 5.00 |  | 3.00 | 1.00 |  |  |  |
| C12–15 alkylbenzoate | 3.50 |  |  |  | 6.50 | 4.00 |  |  |
| Cocoglycerides |  | 3.00 |  | 3.00 |  | 2.50 |  | 3.50 |
| Dicaprylyl ether | 4.00 |  |  |  |  |  |  |  |
| Butylene glycol dicaprylate/Dicaprate |  | 4.00 |  | 3.00 |  |  |  |  |
| Dicaprylyl carbonate |  |  |  | 0.50 |  |  |  | 6.00 |
| Dibutyl adipate |  |  | 2.50 |  |  | 3.00 |  | 1.00 |
| Phenyltrimethicone | 2.00 |  |  |  |  | 3.00 |  |  |
| Cyclomethicone |  | 3.00 |  |  |  |  |  | 4.00 |
| Ethylgalactomannan (N-Hance ® AG-200) |  | 0.50 | 3.50 |  | 2.00 |  |  |  |
| Hydrogenated cocoglycerides |  |  |  | 3.00 | 4.00 |  |  | 2.50 |
| Abil ® Wax 2440 |  |  |  |  |  | 1.50 | 3.00 |  |
| PVP hexadecene copolymer |  |  |  | 1.00 | 1.50 |  |  |  |
| Glycerol | 10.0 | 5.00 |  | 7.50 |  |  |  |  |
| Tocopherol | 1.00 |  |  | 0.75 | 0.50 |  | 1.00 |  |
| Shea butter |  | 2.00 | 3.50 |  |  |  |  | 0.50 |
| Iodopropyl butylcarbamate | 0.12 |  |  |  | 0.20 | 0.15 |  |  |
| DMDM hydantoin |  |  |  | 0.10 |  |  |  |  |
| Methylparaben |  | 0.50 | 0.25 |  | 0.45 |  |  |  |
| Phenoxyethanol | 0.50 | 0.40 |  | 1.00 |  |  |  | 1.00 |
| Octoxyglycerol |  | 0.30 |  |  | 1.00 |  |  |  |
| Ethanol |  |  |  | 2.00 |  |  | 7.50 | 4.00 |
| Trisodium EDTA |  | 0.40 |  | 0.15 |  | 0.20 |  | 0.50 |
| Perfume | 0.20 |  | 0.20 | 0.20 | 0.45 |  |  | 0.20 |
| Water | ad 100 | ad 100 | ad 100 | ad 100 | ad 100 | ad 100 | ad 100 | ad 100 |

The invention claimed is:

1. A cosmetic or dermatological formulation, comprising:
 (a) at least one oxidation-sensitive or UV-sensitive active ingredient;
 (b) at least one dialkyl naphthalate which is distinguished by the structural formula

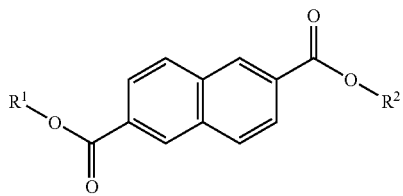

in which where $R^1$ and $R^2$, independently of one another, are chosen from the group of branched and unbranched alkyl groups having 6 to 24 carbon atoms, and
 (c) at least one thickener selected from the group consisting of waxes and oils, the at least one thickener is present in an amount from 0.1 to 30% by weight, based on the total weight of the formulation.

2. The formulation as claimed in claim 1, wherein the at least one dialkyl naphthalate is present in an amount from 0.001 to 30% by weight, based on the total weight of the formulation.

3. The formulation as claimed in claim 1, wherein the at least one dialkyl naphthalate is present in an amount from 0.01 to 20% by weight, based on the total weight of the formulation.

4. The formulation as claimed in claim 1, wherein the at least one dialkyl naphthalate is present in an amount from 1 to 15% by weight, based on the total weight of the formulation.

5. The formulation as claimed in claim 1, wherein at least one of $R^1$ and $R^2$ is a branched alkyl group having 6 to 10 carbon atoms.

6. The formulation as claimed in claim 1, wherein $R^1$ and $R^2$ are branched alkyl groups having 6 to 10 carbon atoms.

7. The formulation as claimed in claim 1, wherein the at least one dialkyl naphthalate includes diethylhexyl naphthalate.

8. The formulation as claimed in claim 1, wherein the at least one oxidation-sensitive or UV-sensitive active ingredient includes 4-(tert-butyl)-4'-methoxydibenzoylmethane.

9. The formulation as claimed in claim 1, wherein the at least one oxidation-sensitive or UV-sensitive active ingredient includes at least one oxidation-sensitive or UV-sensitive active ingredient selected from the group consisting of lipophilic active ingredients.

10. The formulation as claimed in claim 1, wherein the at least one oxidation-sensitive or UV-sensitive active ingredient includes at least one oxidation-sensitive or UV-sensitive active ingredient selected from the group consisting of coenzyme Q10, vitamin A and derivatives thereof, vitamin E and derivatives thereof, lipoic acid and derivatives thereof and carotenoids.

11. The formulation as claimed in claim 10, wherein the at least one oxidation-sensitive or UV-sensitive active ingredient includes vitamin E or derivatives thereof.

12. The formulation as claimed in claim 1, further comprising at least one UV filter substance selected from the group consisting of triazines, benzotriazoles, UV filters liquid at room temperature, organic pigments and inorganic pigments.

13. The formulation as claimed in claim 1, further comprising at least one UV-A filter substance or broadband filter selected from the group consisting of 2,4-bis{[4-(2-ethylhexyloxy)-2-hydroxy]phenyl}-6-(4-methoxy- phenyl)-1,3,5-triazine, phenylene-1,4-bis(2-benzimidazyl)-3,3'-5,5'-tetras-ulfonic acid bis-sodium salt, benzene-1,4-di(2-oxo-3-bornylidenemethyl-10—sulfonic acid, 2-(2H-benzotriazol-2-yl)-4-methyl-6-[2-methyl-3-[1,3,3,3-te-tramethyl-1-[(trimethylsilyl)oxy]disiloxanyl]propyl]phenol, and mixtures thereof.

14. The formulation as claimed in claim 1, further comprising at least one flavone glycoside.

15. The formulation as claimed in claim 14, wherein the at least one flavone glycoside includes α-alpha-glucosylrutin.

16. The formulation as claimed in claim 1, wherein the at least one thickener includes a natural wax of animal or plant origin.

17. The formulation as claimed in claim 16, wherein the natural wax is an insect wax.

18. The formulation as claimed in claim 17, wherein the insect wax is selected from the group consisting of beeswax, shellac wax, Chinese wax and bumblebee wax.

19. The formulation as claimed in claim 16, wherein the natural wax is a plant wax selected from the group consisting of candelilla wax, carnauba wax, Japan wax, esparto grass wax, cork wax, rice wax, sugar cane wax, fruit waxes, flower waxes, leaf waxes from conifers, coffee wax, flax wax, sesame wax, jojoba oil and the like.

20. The formulation as claimed in claim 1, wherein the at least one thickener includes a chemically modified wax or synthetic wax.

21. The formulation as claimed in claim 1, wherein the at least one thickener includes an ester wax.

22. The formulation as claimed in claim 1, wherein the at least one thickener includes a glyceride or triglyceride.

23. The formulation as claimed in claim 1, wherein the at least one thickener includes shea butter.

24. The formulation as claimed in claim 1, wherein the at least one thickener includes a wax selected from the group consisting of behenyl alcohol, cetearyl alcohol, cetyl alcohol, stearyl alcohol, cetyl arachidol and 2-tetradecyloctadecanol.

25. The formulation as claimed in claim 1, wherein the at least one thickener includes a metal soap.

26. The formulation as claimed in claim 25, wherein the metal soap is selected from the group consisting of aluminum stearate and magnesium stearate.

27. The formulation as claimed in claim 1, wherein the thickener is an oil thickener selected from the group consisting of bentonites and hectorites.

28. The formulation as claimed in claim 1, wherein the at least one thickener is selected from the group consisting of ozokerite, ceresine, X-ray amorphous silicon dioxide, hydroxyalkylated guar gum, alkylated guar galactomannans and ethyl galactomannans.

29. The formulation as claimed in claim 1, wherein the at least one thickener is present in an amount from 0.5 to 15% by weight, based on the total weight of the formulation.

30. A method for moisturizing skin, comprising applying to the skin a cosmetic or dermatological formulation, comprising:
(a) at least one oxidation-sensitive or UV-sensitive active ingredient;
(b) at least one dialkyl naphthalate which is distinguished by the structural formula

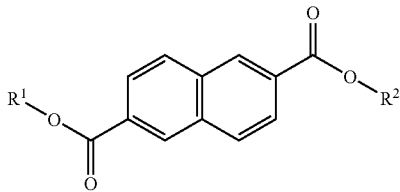

in which where $R^1$ and $R^2$, independently of one another, are chosen from the group of branched and unbranched alkyl groups having 6 to 24 carbon atoms, and
(c) at least one thickener selected from the group consisting of waxes and oils, the at least one thickener is present in an amount from 0.1 to 30% by weight, based on the total weight of the formulation.

31. A method for protecting the skin against photoinduced skin aging, comprising applying to the skin a cosmetic or dermatological formulation, comprising:
(a) at least one oxidation-sensitive or UV-sensitive active ingredient;

(b) at least one dialkyl naphthalate which is distinguished by the structural formula

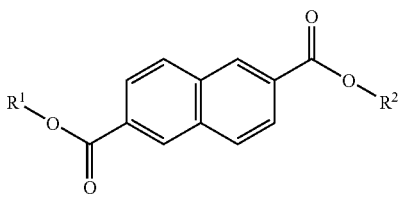

in which where $R^1$ and $R^2$, independently of one another, are chosen from the group of branched and unbranched alkyl groups having 6 to 24 carbon atoms, and (c) at least one thickener selected from the group consisting of waxes and oils, the at least one thickener is present in an amount from 0.1 to 30% by weight, based on the total weight of the formulation.

32. A method for stabilizing cosmetic or dermatological active ingredients against decomposition induced by UV radiation, comprising adding to an active ingredient-containing cosmetic or dermatological formulation (a) at least one dialkyl naphthalate which is distinguished by the structural formula

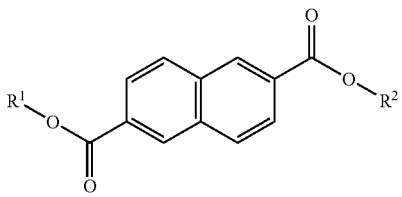

in which where $R^1$ and $R^2$, independently of one another, are chosen from the group of branched and unbranched alkyl groups having 6 to 24 carbon atoms, and (b) at least one thickener selected from the group consisting of waxes and oils, the at least one thickener is present in an amount from 0.1 to 30% by weight, based on the total weight of the formulation.

33. A method for improving the effectiveness and increasing the stability of lipophilic active ingredients in cosmetic or dermatological preparations, comprising adding to an lipophilic active ingredient-containing cosmetic or dermatological formulation (a) at least one dialkyl naphthalate which is distinguished by the structural formula

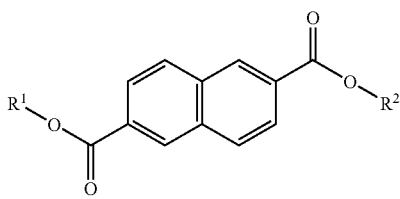

in which where $R^1$ and $R^2$, independently of one another, are chosen from the group of branched and unbranched alkyl groups having 6 to 24 carbon atoms, and (b) at least one thickener selected from the group consisting of waxes and oils, the at least one thickener is present in an amount from 0.1 to 30% by weight, based on the total weight of the formulation.

\* \* \* \* \*